(12) United States Patent
Konings

(10) Patent No.: US 11,298,175 B2
(45) Date of Patent: Apr. 12, 2022

(54) ASYMMETRIC BALANCED WAVEFORM FOR AC CARDIAC IRREVERSIBLE ELECTROPORATION

(71) Applicant: UMC Utrecht Holding B. V., Utrecht (NL)

(72) Inventor: Maurits K. Konings, Utrecht (NL)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 1006 days.

(21) Appl. No.: 15/152,873

(22) Filed: May 12, 2016

(65) Prior Publication Data
US 2016/0331441 A1 Nov. 17, 2016

Related U.S. Application Data

(60) Provisional application No. 62/160,237, filed on May 12, 2015.

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1492* (2013.01); *A61N 1/327* (2013.01);
(Continued)

(58) Field of Classification Search
CPC ...... A61B 2018/00613; A61B 18/1206; A61B 18/1492; A61B 2018/1266;
(Continued)

(56) References Cited

U.S. PATENT DOCUMENTS 6,542,778 B1 4/2003 Fuhr et al.
6,546,270 B1 4/2003 Goldin et al.
(Continued)

FOREIGN PATENT DOCUMENTS

JP 2002-065626 A 3/2002

OTHER PUBLICATIONS

Smith, Kyle C et al. "Model of creation and evolution of stable electropores for DNA delivery." Biophysical journal vol. 86,5 (2004): 2813-26. <https://www.ncbi.nlm.nih.gov/pmc/articles/PMC1304151/> (Year: 2004).*

*Primary Examiner* — Jaymi E Della
*Assistant Examiner* — Sean W Collins
(74) *Attorney, Agent, or Firm* — Dykema Gossett PLLC

(57) ABSTRACT

An electroporation therapy apparatus method, and system is provided. The apparatus, system, and method comprise an electroporation generator (26). The electroporation generator (26) is configured to output an asymmetric balanced waveform to a medical device, and the asymmetric balanced waveform comprises a first positive phase and a first negative phase. The first positive phase comprises a first current and a first time and the first negative phase comprises a second current and a second time. The first current is greater than the second current and the second time is greater than the first time. The asymmetric balanced waveform is configured to irreversibly electroporate a target tissue.

20 Claims, 3 Drawing Sheets

(51) Int. Cl.
*A61N 1/32* (2006.01)
*A61B 18/00* (2006.01)

(52) U.S. Cl.
CPC ............... *A61B 2018/00351* (2013.01); *A61B 2018/00577* (2013.01); *A61B 2018/00613* (2013.01); *A61B 2018/00642* (2013.01); *A61B 2018/00839* (2013.01); *A61B 2018/1266* (2013.01)

(58) Field of Classification Search
CPC ........... A61B 2018/00839; A61B 2018/00642; A61B 2018/00577; A61B 2018/00351; A61N 1/327
See application file for complete search history.

(56) References Cited

U.S. PATENT DOCUMENTS

| | | | |
|---|---|---|---|
| 7,263,397 | B2 | 8/2007 | Hauck et al. |
| 8,221,411 | B2 | 7/2012 | Francischelli et al. |
| 9,289,606 | B2 | 3/2016 | Paul et al. |
| 2002/0111618 | A1* | 8/2002 | Stewart ............... A61B 18/1492 606/41 |
| 2007/0010737 | A1* | 1/2007 | Harvey ................ A61B 5/6874 600/416 |
| 2008/0058706 | A1* | 3/2008 | Zhang .................... A61N 1/327 604/21 |
| 2010/0023004 | A1 | 1/2010 | Francischelli et al. |
| 2010/0069921 | A1 | 3/2010 | Miller et al. |
| 2012/0059255 | A1 | 3/2012 | Paul et al. |
| 2012/0109122 | A1 | 5/2012 | Arena et al. |
| 2013/0030430 | A1 | 1/2013 | Stewart et al. |
| 2014/0052126 | A1* | 2/2014 | Long .................. A61B 18/1206 606/34 |
| 2015/0073401 | A1 | 3/2015 | Kreindel |
| 2017/0266438 | A1* | 9/2017 | Sano .................. A61B 18/1477 |

\* cited by examiner

ASYMMETRIC BALANCED WAVEFORM FOR AC CARDIAC IRREVERSIBLE ELECTROPORATION

CROSS-REFERENCE TO RELATED APPLICATIONS

This application claims the benefit of U.S. provisional application No. 62/160,237, filed 12 May 2015, which is hereby incorporated by reference as though fully set forth herein.

BACKGROUND a. Field

The instant invention relates generally to a system for electrically isolating cardiac tissue.

b. Background Art

It is generally known that ablation therapy may be used to treat various conditions afflicting the human anatomy. One such condition that ablation therapy finds a particular application is in the treatment of atrial arrhythmias, for example. When tissue is ablated, or at least subjected to ablative energy generated by an ablation generator and delivered by an ablation catheter, lesions form in the tissue. Electrodes mounted on or in ablation catheters are used to create tissue necrosis in cardiac tissue to correct conditions such as atrial arrhythmia (including, but not limited to, ectopic atrial tachycardia, atrial fibrillation, and atrial flutter). Arrhythmia (i.e., irregular heart rhythm) can create a variety of dangerous conditions including loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

One candidate for use in therapy of cardiac arrhythmias is electroporation. Electroporation therapy involves electric-field induced pore formation on the cell membrane. The electric field may be induced by applying a direct current (DC) signal delivered as a relatively short duration pulse which may last, for instance, from a nanosecond to several milliseconds. Such a pulse may be repeated to form a pulse train. The electric field may also be induced by applying an alternating current (AC) signal delivered as a relatively short duration pulse which may last, for instance, from a nanosecond to several milliseconds. When such an electric field is applied to tissue in an in vivo setting, the cells in the tissue are subjected to transmembrane potential, which essentially opens up the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) are used to transfect high molecular weight therapeutic vectors into the cells. In other therapeutic applications, a suitably configured pulse train alone may be used to cause cell destruction, for instance by causing irreversible electroporation.

The foregoing discussion is intended only to illustrate the present field and should not be taken as a disavowal of claim scope.

BRIEF SUMMARY

In one embodiment, an electroporation therapy apparatus comprises an electroporation generator. The electroporation generator is configured to output an asymmetric balanced waveform to a medical device. The asymmetric balanced waveform can comprise a first positive phase and a first negative phase. The first positive phase can comprise a first current and a first time and the first negative phase can comprise a second current and a second time. The first current is greater than the second current and the second time is greater than the first time. The asymmetric balanced waveform is configured to irreversibly electroporate a target tissue.

In another embodiment, a method of applying irreversible electroporation to a target tissue can comprise sending an asymmetric balanced waveform from an electroporation generator to a medical device. The asymmetric balanced waveform can comprise a first positive phase and a first negative phase. The first positive phase comprises a first current and a first time and the first negative phase comprises a second current and a second time. The first current is greater than the second current and the second time is greater than the first time. The asymmetric balanced waveform is configured to irreversibly electroporate a target tissue.

In yet another embodiment, an electroporation therapy system can comprise a medical device comprising at least one electrode, and an electroporation generator. The electroporation generator is configured to output an asymmetric balanced waveform to the at least one electrode of the medical device. The asymmetric balanced waveform comprises a first positive phase and a first negative phase. The first positive phase comprises a first current and a first time and the first negative phase comprises a second current and a second time. The first current is greater than the second current and the second time is greater than the first time. The asymmetric balanced waveform is configured to irreversibly electroporate a target tissue.

DETAILED DESCRIPTION OF EMBODIMENTS

Figure 1:
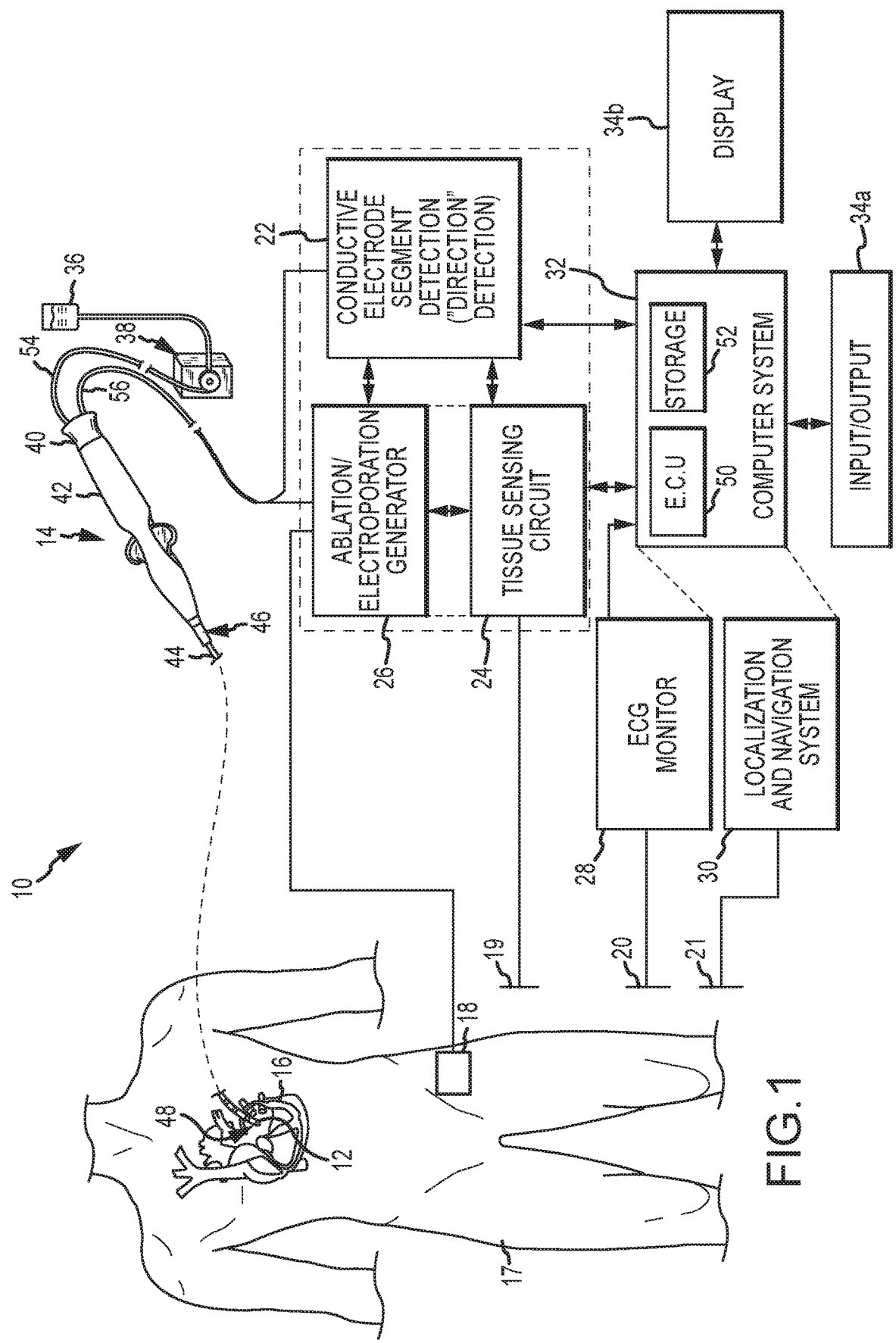
FIG. 1 is a schematic and block diagram view of a system incorporating embodiments for electroporation therapy.

Referring now to the drawings wherein like reference numerals are used to identify identical components in the various views, FIG. 1 is a diagrammatic and block diagram view of a system 10 in connection with which electrode assemblies for electroporation therapy may be used. In general, the various embodiments include an electrode assembly disposed at the distal end of a catheter. The electrode assembly can comprise a plurality of individual, electrically-isolated electrode elements. Each electrode element can be individually wired such that it can be selectively paired or combined with any other electrode element to act as a bipolar or a multi-polar electrode for both sensing (more below) and electroporation energization purposes. In the sensing mode, the electrode elements can be electrically scanned to detect or identify which electrode elements (or pairs) have electrical conduction characteristics indicative of contact with the target tissue (e.g., impedance, phase angle, reactance). Once such electrode elements have been identified, an electroporation generator can be controlled to energize the identified electrode elements in accordance with an electroporation energization strategy. The selective energization can improve selectivity of the target tissue, more effectively directing the therapy to just the desired, target tissue.

Irreversible Electroporation (IRE) of cells is an important technique for producing precisely targeted lesions in, for example, the heart. During application of the high intensity currents to produce such lesions, it is desirable to avoid muscle contractions. If the applied current is a DC (or low frequency) current, then severe muscle contractions can occur because the excitation threshold for excitable tissues (muscle cells and neurons) is much lower than the threshold for electroporation. Therefore, in the case of applied DC current for electroporation, anesthesia may be needed for muscle relaxation. In order to avoid the need for anesthesia and/or muscle relaxants, one can apply a high frequency alternating current. The present disclosure provides manners and solutions for producing sufficient tissue necrosis without the need for anesthesia and muscle relaxants to avoid (skeletal) muscle spasms as result of the applied currents.

The particular energization strategy chosen will depend on the particular type of electroporation therapy sought to be achieved. Exemplary electroporation therapies include: (1) electroporation-mediated therapy; (2) electroporation-induced primary necrosis therapy; and (3) electric field-induced apoptosis (or secondary necrosis) therapy. Each therapy will be described below.

Electroporation-mediated ablation therapy refers to delivering tissue pre-conditioning effects using electroporation. Pre-conditioning effects would lead to altering the biophysical properties of the tissue which would make the tissue receptive to other ablative therapies such as radio-frequency (RF), ultrasound, and photodynamic therapy. Tissue pre-conditioning may be achieved by delivering electrolytes to the tissue locally using electroporation, thereby changing the biophysical properties of the tissue such as its electrical, acoustical, optical, thermal, and perfusion properties. In this case, the electric field applied to the tissue causes transient and reversible effects of temporarily opening the pores on the cell wall, and the cell remains viable after the application of the electric field. In general, electroporation will involve the application of direct current (DC) or alternating current (AC) to create an electric field sufficient to "tear" the lipid bilayer that forms the cell membrane. There are many voltage level/pulse duration/duty cycle combinations that may be effective. It should be understood that a plurality of factors may affect the particular energization scheme needed to achieve the temporary (i.e., transient and reversible) opening of pores on the cell wall, including species, tissue size, cell size and development stage.

Electroporation-induced primary necrosis therapy refers to the effects of delivering electrical current in such manner as to directly cause an irreversible loss of plasma membrane (cell wall) integrity leading to its breakdown and cell necrosis. This mechanism of cell death may be viewed as an "outside-in" process, meaning that the disruption of the outside wall of the cell causes detrimental effects to the inside of the cell. Typically, for classical plasma membrane electroporation, electric current is delivered as a pulsed electric field in the form of short-duration direct current (DC) pulses (e.g., 0.1 to 20 ms duration) between closely spaced electrodes capable of delivering a relatively low electric field strength of about 0.1 to 1.0 kV/cm. As discussed herein, an asymmetrical balanced waveform can also be used with AC waveforms as further described below.

Electric-field-induced apoptosis (or secondary necrosis) therapy refers to the effects of delivering electrical current in such a manner as to cause electromanipulation of the intracellular structures (e.g., such as the nucleus, mitochondria or endoplasmic reticulum) and intracellular functions that precede the disassembly of the cell and irreversible loss of plasma membrane (cell wall). This mechanism of cell death may be viewed as an "inside-out" process, meaning that the disruption of the inside of the cell causes detrimental "secondary" effects to the outside wall of the cell. For electric field-induced apoptosis, electric current is delivered as a pulsed electric field in the form of extremely short-duration DC pulses (e.g., 1 to 300 ns duration) between closely spaced electrodes capable of delivering a relatively high electric field strength of about 2 to 300 kV/cm. As discussed herein, an asymmetrical balanced waveform can also be used with alternating current to induce electric-field-induced apoptosis using the m further described below.

It should be understood that while the energization strategies for electroporation-mediated ablation therapy, electroporation-induced primary necrosis therapy, electric-field-induced apoptosis (or secondary necrosis) therapy are described as involving DC pulses and AC waveforms, embodiments may use variations and remain within the spirit and scope of the invention. For example, exponentially-decaying pulses, exponentially-increasing pulses, mono-phase or bi-phase pulses and combinations of one or more all may be used.

The electroporation embodiments described and depicted herein can involve two different modes of therapy: (1) usage of electroporation therapy to destroy tissue (i.e., cell death) and (2) electroporation-mediated therapy where electroporation mechanism is used to modify a tissue property (e.g., conductivity, reactance, responsiveness/irresponsiveness to photonic energy, responsiveness/irresponsiveness to ultrasonic energy, etc.) for subsequent tissue sensing and/or ablation (e.g., via electrical tissue sensing or electrical energy delivery such as RF energy deliver, via photodynamic-based sensing and/or energy delivery, via ultrasound-based sensing and/or energy delivery, etc.).

As to the first mode of therapy mentioned above (i.e., electroporation alone), it should be understood that electroporation is not substantially energy-dissipative and thus does not substantially thermally alter the target tissue (i.e., does not substantially raise its temperature), thereby avoiding possible thermal effects (e.g., possible pulmonary vein stenosis when using RF energy for a pulmonary vein isolation (PVI) procedure). Even to the extent that RF energy based ablation is used only as a "touch up" after an initial round of electroporation therapy, the thermal effects are reduced due to the corresponding reduction in the application of RF energy. This "cold therapy" thus has desirable characteristics.

As to the second mode mentioned above (i.e., electroporation-mediated therapy), electrochromic dyes may be used for effective monitoring of the progress of and completion of electroporation therapy to condition the target tissue. In the first mode, however, the use of electrochromic dyes do not come into play.

With this background, and now referring again to FIG. 1, the system 10 includes a multi-polar or multi-array catheter electrode assembly 12 configured to be used as briefly outlined above and as described in greater detail below. The electrode assembly 12 is incorporated as part of a medical device such as a catheter 14 for electroporation therapy of tissue 16 in a body 17 of a patient. In the illustrative embodiment, the tissue 16 comprises heart or cardiac tissue. It should be understood, however, that embodiments may be used to conduct electroporation therapy with respect to a variety of other body tissues.

FIG. 1 further shows a plurality of patch electrodes designated 18, 19, 20 and 21, which are diagrammatic of the body connections that may be used by the various sub-systems included in the overall system 10, such as a detector 22, a tissue sensing circuit 24, an energization generator 26 (e.g., electroporation and/or ablation depending on the embodiment), an EP monitor such as an ECG monitor 28 and a localization and navigation system 30 for visualization, mapping and navigation of internal body structures. It should be understood that the illustration of a single patch electrode is diagrammatic only (for clarity) and that such sub-systems to which these patch electrodes are connected may, and typically will, include more than one patch (body surface) electrode. The system 10 may further include a main computer system 32 (including an electronic control unit 50 and data storage-memory 52), which may be integrated with the system 30 in certain embodiments. The system 32 may further include conventional interface components, such as various user input/output mechanisms 34*a* and a display 34*b*, among other components.

The detector 22 is coupled to the plurality of electrode elements of the electrode assembly 12 and in one embodiment is configured to identify which elements have characteristics (e.g., if electrical characteristics, then for example, impedance, phase angle, reactance, etc.) indicative of contact of the electrode element with tissue 16. In embodiments where the electrode elements cover up to 360 degrees (e.g., a distal tip in hemispherical shape or circular catheter with multiple electrodes), it is desirable to energize only those electrode elements that are in contact with tissue, as described above. This may be thought of as a "direction-sensitive" since determining what electrode elements are in contact with tissue also determines the "direction" of the therapy to be delivered to the tissue.

A tissue sensing circuit 24 may be used in connection with the detector 22 for determining an characteristic (e.g., electrical characteristic) to be used in making a "contact" versus "no contact" decision for each electrode element (or pair thereof). In an embodiment, the detector 22 may be configured to scan (probe) the electrode elements (or pairs) and record the identification of such in-contact electrode elements. The detector 22, the tissue sensing circuit 24 and the generator 26 are enclosed in a dashed-line box in FIG. 1 to indicate the contemplated cooperation necessary to perform the functions described herein. However, it should be understood that no necessary physical integration is implied (i.e., these blocks may be embodied as physically separate components). More particularly, any one of the detector 22, the tissue sensing circuit or the generator 26 may be implemented as a stand-alone component or may be implemented in another portion of system 10 provided such other portion has adequate capabilities to perform the desired function(s).

The tissue sensing circuit 24 as noted above is configured to determine an electrical characteristic associated with an electrode element or pair for purposes of determining whether the electrode element (or pair) is in contact with the tissue 16. The characteristic, when electrical in nature, may be an impedance, a phase angle, a reactance or an electrical coupling index (ECI), as seen by reference to co-pending U.S. patent application Ser. No. 12/622,488, filed Nov. 20, 2009 entitled "SYSTEM AND METHOD FOR ASSESSING LESIONS IN TISSUE", owned by the common assignee of the present invention and hereby incorporated by reference in its entirety. In such an embodiment, multiple skin patch electrodes may be used. Skin (body surface) patch electrodes may be made from flexible, electrically conductive material and are configured for affixation to the body 17 such that the electrodes are in electrical contact with the patient's skin. In one embodiment, the circuit 24 may comprise means, such as a tissue sensing signal source (not shown), for generating an excitation signal used in impedance measurements (e.g., the excitation signal being driven through the subject electrode element) and means, such as a complex impedance sensor (not shown), for determining a complex impedance or for resolving the detected impedance into its component parts. Other patch electrodes (shown only diagrammatically as electrode 19) may preferably be spaced relatively far apart and function as returns for an excitation signal generated by the tissue sensing circuit 24 (as described in U.S. application Ser. No. 12/622,488). As to spacing, tissue sensing patch electrodes (shown only diagrammatically as electrode 19) may be two in number located respectively on the medial aspect of the left leg and the dorsal aspect of the neck or may alternatively be located on the front and back of the torso or in other conventional orientations. Of course, other implementations are possible.

The detector 22 may receive the measured characteristic from tissue sensing circuit 24 and then determine whether the subject electrode element is in tissue contact based on the value of the determined electrical characteristic, along with predetermined threshold data and decision rules (e.g., if computer-implemented, programmed rules). As shown, the tissue sensing circuit 24 may be coupled through the generator 26 and may use the same conductors to the electrode assembly 12 for excitation purposes as used by the generator 26 for energization purposes. In other embodiments, the system can determine whether the electrode elements, or other portions of the medical device, are in contact with a tissue or other object within an area of interest through mechanical force sensors, optical force sensors, or other sensors as would be known to one of ordinary skill in the art.

The electroporation generator 26 is configured to energize the identified electrode elements in accordance with an electroporation energization strategy, which may be predetermined or may be user-selectable. The generator 26 may be configured to communicate with the detector 22 to receive a signal or data set indicative of the electrode elements previously identified during the scanning phase as being in tissue contact. The electroporation energizing strategies (e.g., bi-poles, multi-poles, pulse magnitude, number and duration, etc.) are defined based on their correspondence to a respective one of the electroporation therapies described above, namely: (1) electroporation-mediated therapy; (2) electroporation-induced primary necrosis therapy; and (3) electric field-induced apoptosis (or secondary necrosis) therapy.

For electroporation-mediated therapy, the generator 26 may be configured to produce an electric current that is delivered via the electrode assembly 12 as a pulsed electric field in the form described above. In another embodiment, the generator 26 may be configured to produce an electric current that is delivered via the electrode assembly 12 as an alternating electric field that comprises an asymmetric balanced waveform as further described below.

For electroporation-induced primary necrosis therapy, the generator 26 may be configured to produce an electric current that is delivered via the electrode assembly 12 as a pulsed electric field in the form of short-duration direct current (DC) pulses (e.g., 0.1 to 20 ms duration) between closely spaced electrodes capable of delivering a relatively low electric field strength (i.e., at the tissue site) of about 0.1 to 1.0 kV/cm. In another embodiment, the generator 26 may be configured to produce an electric current that is delivered via the electrode assembly 12 as an alternating electric field that comprises an asymmetric balanced waveform as further described below.

For electric field-induced apoptosis therapy, the generator 26 may be configured to produce an electric current that is delivered via the electrode assembly 12 as a pulsed electric field in the form of extremely short-duration direct current (DC) pulses (e.g., 1 to 300 ns duration) between closely spaced electrodes capable of delivering a relatively high electric field strength (i.e., at the tissue site) of about 2 to 300 kV/cm. In another embodiment, the generator 26 may be configured to produce an electric current that is delivered via the electrode assembly 12 as an alternating electric field that that comprises an asymmetric balanced waveform as further described below.

In certain other embodiments (e.g., electroporation-mediated ablation therapy), both electroporation specific energy as well as ablation specific energy can be used in the overall process and in such embodiments, the generator 26 may be further configured to deliver ablation energy as well, or another device may be provided to supply the ablation energy.

For example, in the case of electroporation-mediated ablation therapy (i.e., electroporation to modify tissue characteristics then followed by RF ablation), the generator 26 may be further configured to generate, deliver and control RF energy output by the electrode assembly 12 of the catheter 14. An ablation energizing power source portion of generator 26 may comprise conventional apparatus and approaches known in the art, such as may be found in commercially available units sold under Ampere™ RF Ablation Generator, available from St. Jude Medical™. In this regard, the ablation functional portion of the generator 26 may be configured to generate a signal at a predetermined frequency in accordance with one or more user specified parameters (e.g., power, time, etc.) and under the control of various feedback sensing and control circuitry as is known in the art. For example, the RF ablation frequency may be about 450 kHz or greater, in certain embodiments. Various parameters associated with the ablation procedure may be monitored including impedance, the temperature at the tip of the catheter, ablation energy and the position of the catheter and provide feedback to the clinician regarding these parameters. As to ablation therapy, the electrode 18 may function as an RF indifferent/dispersive return for an RF ablation signal (in certain embodiments).

With continued reference to FIG. 1, as noted above, the catheter 14 may comprise functionality for electroporation and in certain embodiments (i.e., electroporation-mediated ablation therapy) also an ablation function (e.g., RF ablation). It should be understood, however, that in those embodiments, variations are possible as to the type of ablation energy provided (e.g., cryoablation, ultrasound, etc.). For example, the embodiment shown in FIG. 1 includes a fluid source 36 having a biocompatible fluid such as saline or other electrolyte suitable for the electroporation-mediated therapy chosen, which may be delivered through a pump 38 (which may comprise, for example, a fixed rate roller pump or variable volume syringe pump with a gravity feed supply from the fluid source 36 as shown) for delivery of a suitable electrolyte for electroporation-mediated ablation or saline for irrigation.

In the illustrative embodiment, the catheter 14 includes a cable connector or interface 40, a handle 42, a shaft 44 having a proximal end 46 and a distal 48 end. As used herein, "proximal" refers to a direction toward the end of the catheter near the clinician and "distal" refers to a direction away from the clinician and (generally) inside the body of a patient. The catheter 14 may also include other conventional components not illustrated herein such as a temperature sensor, additional electrodes, and corresponding conductors or leads. The connector 40 provides mechanical, fluid and electrical connection(s) for cables 54, 56 extending from the pump 38 and the generator 24. The connector 40 may comprise conventional components known in the art and as shown may is disposed at the proximal end of the catheter 14.

The handle 42 provides a location for the clinician to hold the catheter 14 and may further provide means for steering or the guiding shaft 44 within the body 17. For example, the handle 42 may include means to change the length of a guidewire extending through the catheter 14 to the distal end 48 of the shaft 44 or means to steer the shaft 44. The handle 42 is also conventional in the art and it will be understood that the construction of the handle 42 may vary. In an alternate exemplary embodiment, the catheter 14 may be robotically driven or controlled. Accordingly, rather than a clinician manipulating a handle to advance/retract and/or steer or guide the catheter 14 (and the shaft 44 thereof in particular), a robot is used to manipulate the catheter 14.

The shaft 44 is an elongated, tubular, flexible member configured for movement within the body 17. The shaft 44 is configured to support the electrode assembly 12 as well as contain associated conductors, and possibly additional electronics used for signal processing or conditioning. The shaft 44 may also permit transport, delivery and/or removal of fluids (including irrigation fluids and bodily fluids), medicines, and/or surgical tools or instruments. The shaft 44 may be made from conventional materials such as polyurethane and defines one or more lumens configured to house and/or transport electrical conductors, fluids or surgical tools. The shaft 44 may be introduced into a blood vessel or other structure within the body 17 through a conventional introducer. The shaft 44 may then be advanced/retracted and/or steered or guided through the body 17 to a desired location such as the site of the tissue 16, including through the use of guidewires or other means known in the art.

The localization and navigation system 30 may be provided for visualization, mapping and navigation of internal body structures. The system 30 may comprise conventional apparatus known generally in the art (e.g., an EnSite™ NavX™ Navigation and Visualization System, commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference). It should be understood, however, that this system is exemplary only and not limiting in nature. Other technologies for locating/navigating a catheter in space (and for visualization) are known, including for example, the CARTO navigation and location system of Biosense Webster, Inc., the AURORA® system of Northern Digital Inc., commonly available fluoroscopy systems, or a magnetic location system such as the gMPS system from St. Jude Medical, Inc. In this regard, some of the localization, navigation and/or visualization system would involve a sensor be provided for producing signals indicative of catheter location information, and may include, for example one or more electrodes in the case of an impedance-based localization system, or alternatively, one or more coils (i.e., wire windings) configured to detect one or more characteristics of a magnetic field, for example in the case of a magnetic-field based localization system. Further discussion regarding other embodiments of systems and medical devices that can be used in an electroporation system can be found in U.S. Pat. No. 9,289,606, filed 2 Sep. 2010, the entire disclosure of which is incorporated by reference as though fully set forth herein.

When using an AC waveform, the present disclosure provides, among other things, an asymmetric balanced waveform designed in such a way that electroporation is enhanced in a non-linear way, and at the same time, no net low frequency components are produced. This asymmetric balanced waveform is able to cause electroporation in the tissues of the heart, without producing unwanted side-effects such as (skeletal) muscle contraction.

It is possible to produce irreversible electroporation with a high frequency asymmetrical, balanced electromagnetic current without muscle contraction in view of different time constants that are associated with the various processes involved, in combination with the non-linear character of the electroporation as a function of the strength of the current density that is imposed on the membranes of the tissue.

There are two possibilities for cells to undergo irreversible electroporation. One mechanism for a cell to undergo irreversible electroporation comprises rupture of a portion of the cell membrane. This essentially creates permanent hole within the membrane. The second mechanism for a cell to undergo irreversible electroporation comprises lysis as a consequence of chemical imbalances caused by molecular transport through transient pores. This can also be known as a secondary process to electroporation. Rupture is believed to be prompt and can occur within 100 microseconds after a large applied pulse. However, it has also been shown that rupture is a stochastic process. At lower intensities of the applied electric field, the second mechanism dominates.

Within the framework of finding an optimal waveform for the applied current in order to achieve local cardiac electroporation without significant muscle contraction, the following five key concepts are of specific interest. The first key concept comprises the stages of the cell membrane while undergoing electroporation. Electroporation comprises three stages. These three stages comprise, charging of the cell membrane, creation of pores, and evolution of larger pore radii. Charging of the cell membrane can occur between 0-0.5 µs, creation of pores can occur between 0.5-1.4 µs, and evolution of larger pore radii can occur between 1.4 µs to 1 ms.

The second concept comprises the proportionality of the new pore creation to the voltage over the membrane. The creation of new pores is proportional to $e^{(\Phi_m)^2}$, in which $\Phi_m$ is the voltage over the membrane. As a result, if N is the number of pores, then $$\frac{d}{dt}N = \alpha e^{\beta(\Phi_m)^2}\left(1 - \frac{N}{N_{FINAL}}\right),$$

in which $\alpha$ and $\beta$ are constants, and $N_{FINAL}$ denotes a theoretical final equilibrium number of pores (for t goes to infinity).

As seen in the above equation, the $\Phi_m$ appears in the form of the square $(\Phi_m)^2$ in the exponent, and therefore, on basis of this non-linearity, the production rate of new pores would be enhanced if the time duration of the transmembrane voltage $\Phi_m$ would be reduced by a factor 2 and amplitude of $\Phi_m$ would be multiplied by a factor 2. As a result, in order to enhance pore formation, it is better to have a higher value of $\Phi_m$ during a shorter period of time that a lower value of $\Phi_m$ that is spread out over a longer period of time. This steep non-linearity corresponds to the "threshold value" of $\Phi_m$, thres≈1 V as proposed in earlier models of pore formation.

The third concept comprises building up the voltage over the membrane. The voltage $\Phi m$ over the membrane is built up during the first stage ("charging of the cell membrane") mentioned above. As a result, substantial formation of pores in the membranes commences only after 0.5 µs.

The fourth concept comprises having the highest values of the applied field always point in the same direction. Formation of aqueous pores can follow a certain scheme, where the formation of the actual aqueous pores is preceded by more subtle stages of alterations in the membrane and initial formation of aqueous pockets that start to penetrate the membrane. It is favorable for early pore formation to have all of the highest values of the applied field over the membrane $E_m = \nabla \Phi_m$ always point in the same direction. In one embodiment, this direction can be from the outside to the inside. In another embodiment, the direction can be from the inside to the outside. Utilizing this concept allows the repetitive series of high values of $\Phi m$ "work in the same direction." This allows the penetrating effect of initial dimples enhance each other.

Figure 2A:
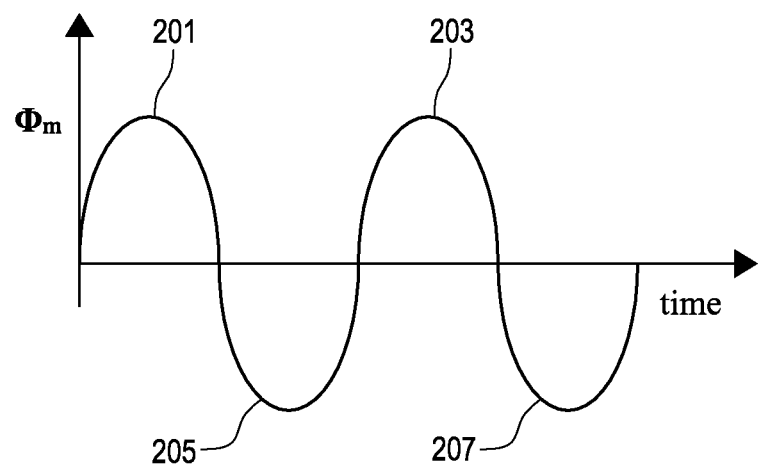
FIG. 2A is a plot of a sinusoidal waveform.
Figure 2B:
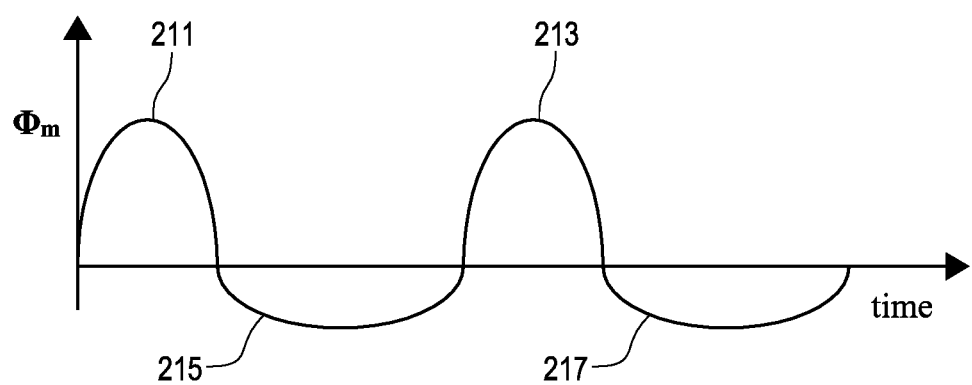
FIG. 2B is a plot of an adapted waveform according to the disclosure.

If $\Phi m(t)$ would be a purely sinusoidal function of time, then such a "constructive series of maximal field strengths" would not take place. This type of sinusoidal function is illustrated in FIG. 2A. FIG. 2A comprises a first positive phase 201, a second positive phase 203, a first negative phase 205, and a second negative phase 207. As the first positive phase and the first negative phase are similar in all ways except direction, a constructive series of maximal field strengths is not achieved. In the alternative, FIG. 2B illustrates an adapted waveform. FIG. 2B comprises a first positive phase 211, a second positive phase 213, a first negative phase 215, and a second negative phase 217. In contrast to FIG. 2A, the first negative phase 215 and the second negative phase 217 of the adapted waveform of FIG. 2B have been flattened and lengthened in time. As a result of this change to the waveform the penetrating effect of initial dimples would enhance each other.

The fifth concept comprises adding a latency period between each positive and negative phase. A short latency period, during which the applied current is zero, can be inserted between each positive and negative phase in FIG. 2 in order to avoid damage to the circuit (e.g., MOSFET) components of the current generator system.

The non-linear character of electroporation when using a high frequency asymmetrical, balanced electromagnetic current can be exploited through several different mechanisms. One mechanism for exploiting the non-linear character of electroporation is using a high frequency. The high frequency can be utilized by applying an AC waveform that contains a fast sequence of alternating "positive" phases and "negative" phases. The strength and the length of each alternating positive and negative phase can be used to further exploit the non-linear characteristic of electroporation. This mechanism can be referred to as an asymmetric waveform. The asymmetric waveform can be achieved by letting the strength of the applied current that flows in one direction (the "positive" direction) be much higher than the strength of the applied current that flows in the opposite direction (the "negative" direction). Another mechanism that can be used to exploit the non-linear characteristic of electroporation is balancing the current imparted to a target tissue during a treatment. This balancing can be achieved by making the "negative" phases last longer than the "positive" phases to compensate for the higher amplitude of the positive phases. The length of the phases can be controlled in such a way that the net current imparted to a target tissue during a treatment, integrated over time, is near or at zero.

Figure 3:
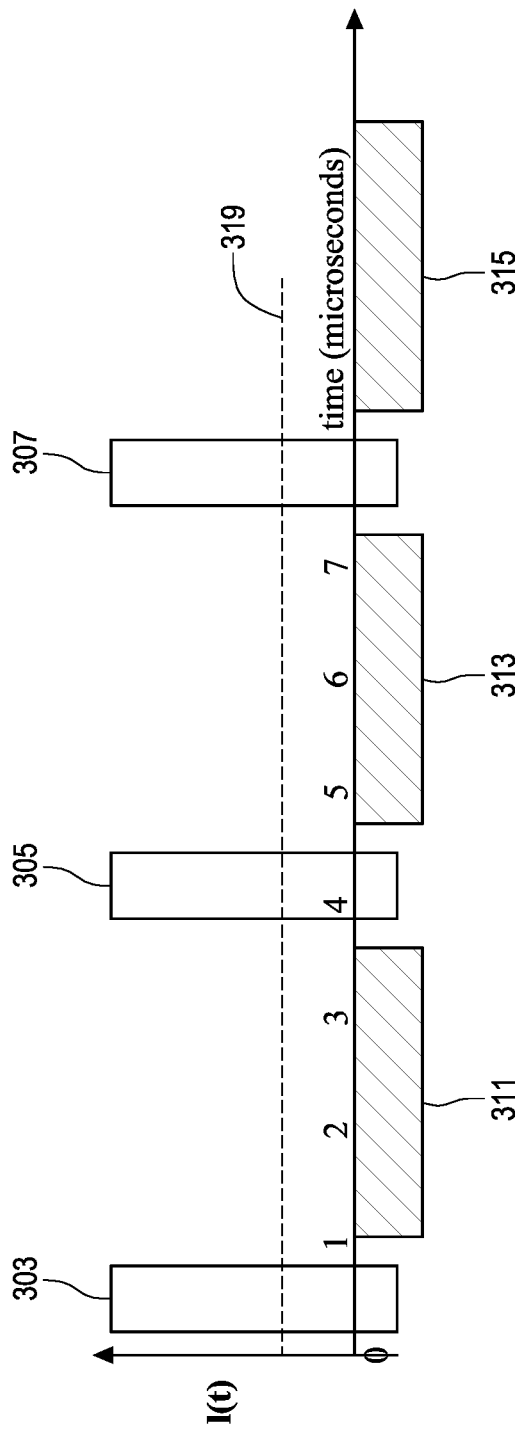
FIG. 3 is a plot of an asymmetric applied current pattern.

FIG. 3 illustrates a high frequency asymmetrical, balanced electromagnetic current pattern as incorporating the mechanisms discussed above. The illustrated high frequency asymmetrical, balanced electromagnetic current pattern 301 depicts a suitable applied current function I(t) as discussed throughout the disclosure. The high frequency asymmetrical, balanced electromagnetic current pattern 301 can comprise a first positive phase 303, a second positive phase 305, a third positive phase 307, a first negative phase 311, a second negative phase 313, a third negative phase 315, and a applied voltage line 319. The first positive phase 303 comprises a first current and a first time. By integrating the first current and the first time, a first net current can be determined. The first negative phase 311 comprises a second current and a second time. By integrating the second current and the second time, a second net current can be determined. The first positive phase 303 and the first negative phase 311 can comprise a cycle. The illustrated embodiment further shows a second positive phase 305 that comprises a third current and a third time, a second negative phase 313 that comprises a fourth current and a fourth time, a third positive phase 307 that comprises a fifth current and a fifth time, and a third negative phase 315 that comprises a sixth current and a sixth time. By integrating the current and the time for each of the phases present in FIG. 3, a net current for each phase can be determined. Each of the pairs of positive phases and negative phases can comprise a separate cycle. While each phase comprises a net current, when the net current of a positive phase and the net current of a paired negative phase (a cycle) are combined, the resulting net current is near or at zero. The applied voltage line 319 illustrates the value of I(t) that produces a voltage of 0.5 Volt over the membrane.

Although the net current, integrated over time, amounts to around or at zero, the net electroporation effect (the "pushing effect of the applied current density on the molecules in the membrane that ultimately leads to a breach (electroporation hole)") does NOT amount to zero. The electroporation effect is the "pushing effect of the applied current density on the molecules in the membrane that ultimately leads to a breach or an electroporation hole. The electroporation effect can be achieved if the amplitude of the positive phase equals a times the amplitude of the negative phase. This results in the "pushing effect on the molecules in the membrane" of the positive phase being much larger than a times the "pushing effect on the molecules in the membrane" of the negative phase.

As a result, even if the duration of the negative phase is a times the duration of the positive phase (such that the net current, integrated over time, is near or at zero), there is still a "build-up" effect of the pushing on the molecules in the membrane in the "positive" direction.

It is possible to produce irreversible electroporation with a high frequency asymmetrical, balanced electromagnetic current without muscle contraction at least because the different time constants that are associated with the various processes involved, in combination with the non-linear character of the electroporation strength as function of the strength of the applied current density field.

As stated previously, muscle contraction during electroporation of a target tissue can be a concern. When looking for the possibility of irreversible electroporation without muscle contraction, it is important to note that the minimum strength of the applied currents needed for activation of excitable tissues (neurons and muscle cells) is much lower than the minimum strength needed for electroporation. Therefore, in order to avoid unwanted muscle contractions, it is important to consider the various time constants $\tau_{chron}$ (chronaxie time) associated with activation of various excitable tissues.

The chronaxie time associated with neurostimulation ranges from about 130 microseconds for thick myelinated fibers (which are present in e.g. the spinal cord), and about 500 microseconds for non-myelinated cells. The threshold for excitation of excitable tissue depends on the frequency of the applied electric field. To determine the threshold for excitation of excitable tissue the following equation can be used.

$$E_{threshold} = E_{rheobase}\left(1 + \frac{\tau_{chron}}{T}\right),$$

in which T=1/f, and f is the frequency of the applied electric field, and in which $E_{rheobase}$ is about 5.4 V/m for thick myelinated fibers, and up to 20 V/m for other cells. The values of $E_{rheobase}$ an be determined by one of ordinary skill in the art. The structure of the last equation can be attributed to an "integrating" effect within time intervals that are shorter than the chronaxie time $\tau_{chron}$:

Further, no neurostimulation takes place under other conditions. To determine whether neurostimulation occurs the following equation can be used.

$$\forall t \in [0, \tau_{chron}]: \int_0^t E_m\, d\tau = \int_0^t \frac{1}{a_m} \Phi_m\, d\tau < S_{threshold},$$

in which $a_m$ is the thickness of the membrane and $S_{threshold}$ is a fixed value related to $E_{rheobase}$.

This equation implies that even at high frequencies, neurostimulation can be provoked if the applied electric field is very large and causes the integral to exceed the threshold within the interval [0, $\tau_{chron}$] viz. within a single positive (or negative) phase (i.e., within 0.5/f) of the applied electric field. This underscores the importance of keeping the intensity of the applied AC waveform as low as possible, even at high frequencies f.

As a result of the above information, a sixth key concept can be added to the five concepts discussed above. The sixth concept comprises obtaining a maximum electroporation while minimizing excitation. To achieve this a maximum electroporation needs to be obtained within minimum $\int_0^t E\, d\tau$.

As discussed above, there are now six key concepts that can be utilized to provide a framework of finding an optimal waveform for the applied current in order to achieve local cardiac electroporation without significant muscle contraction.

First, electroporation consists of three stages: charging of the call cell membrane (0-0.5$\mu_s$), creation of pores (0.5-1.4$\mu_s$), and evolution of larger pore radii (1.4$\mu_s$ to 1 ms).

Therefore, maximization of the creation of pores should take place within time intervals of around 1 microsecond.

Second, the creation rate of new pores is proportional to $e^{(\Phi_m)^2}$. Therefore: the $\Phi_{m(t)}$ should contain relatively high but short peaks.

Third, the repetitive series of high peaks of $\Phi_m$ should "work in the same direction." Therefore: the waveform should be asymmetric, i.e.: the positive (or negative) peaks should be substantially larger in amplitude than the negative (or positive) peaks.

Fourth, a short latency period, during which the applied current is zero, should be inserted between each positive and negative phase in FIG. 3 in order to avoid damage to the MOSFET components of the current generator system.

Fifth, the repair mechanisms within the cells that aim at repairing the electroporation holes, need more that 0.5 seconds to be effective. Therefore, in order to frustrate and counteract these repair mechanisms, the time interval between any two bursts of applied asymmetrical AC waveforms should not exceed 0.5 seconds.

Sixth, maximum electroporation needs to be obtained with minimum $\int_0 E_m d\tau$. Therefore, the integral over time of each single entire period of the periodic function $\Phi_{m(t)}$ should amount up to near or at zero, i.e.: $\int_0^T \Phi_m d\tau=0$, in which T is the duration of one single entire period of the periodic function $\Phi_{m(t)}$. Furthermore, in combination with the fourth concept, this implies that the shallow negative phases in FIG. 2b should be broadened in time to let $\int_0^T \Phi_m d\tau=0$.

In another embodiment, a method of applying electroporation to a target tissue as discussed throughout the disclosure is disclosed. The method can comprise sending an asymmetric balanced waveform from an electroporation generator to a medical device. The asymmetric balanced waveform can comprise a first positive phase and a first negative phase. The first positive phase comprises a first current and a first time and the first negative phase comprises a second current and a second time. The first current is greater than the second current and the second time is greater than the first time. The asymmetric balanced waveform is configured to irreversibly electroporate a target tissue Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An electroporation therapy apparatus, comprising:
an electroporation generator, wherein the electroporation generator is configured to output an asymmetric balanced waveform to a medical device comprising an electrode assembly having a plurality of electrode elements, wherein the electroporation generator is further configured to receive a signal for identifying which pairs of the plurality of electrode elements have electrical characteristics indicative of contact with a target tissue when the target tissue is energized with an excitation signal, and wherein the electroporation generator is configured to use an electroporation energization strategy to energize at least one of the pairs of the plurality of electrode elements identified as having contact with the target tissue with the asymmetric balanced waveform,
wherein the asymmetric balanced waveform comprises a first positive phase and a first negative phase, wherein the first positive phase comprises a first current and a first time and wherein the first negative phase comprises a second current and a second time, wherein the first current is greater than the second current and wherein the second time is greater than the first time, and wherein the asymmetric balanced waveform is configured to irreversibly electroporate the target tissue non-linearly as a function of a variable current density imposed on the target tissue from the first and second currents over the first and second times to enhance the irreversible electroporation, and wherein the asymmetric balanced waveform is further configured to provide a production rate of new pores that is enhanced in a non-linear manner when a time duration of a transmembrane voltage is reduced by a factor 2 and an amplitude of the transmembrane voltage is multiplied by a factor 2.

2. The electroporation therapy apparatus of claim 1, wherein the first positive phase and the first negative phase comprises a cycle and wherein the electroporation generator is configured to output a plurality of cycles to the target tissue.

3. The electroporation therapy apparatus of claim 2, wherein the electroporation generator is configured to insert a latency period between the first positive phase and the first negative phase and between each of the plurality of cycles.

4. The electroporation therapy apparatus of claim 3, wherein the latency period between each of the plurality of cycles is less than 0.5 seconds.

5. The electroporation therapy apparatus of claim 2, wherein combined area of each positive phase and each negative phase in each of the plurality of cycles is near zero.

6. The electroporation therapy apparatus of claim 2, wherein the plurality of cycles is configured to apply an applied current function to the target tissue.

7. The electroporation therapy apparatus of claim 6, wherein the applied current function comprises a value of 0.5 Volts.

8. The electroporation therapy apparatus of claim 1, wherein the electroporation generator is further configured to receive a signal indicative of a tissue state.

9. The electroporation therapy apparatus of claim 8, wherein the electroporation generator is further configured to calculate and set the asymmetric balanced waveform using the received signal.

10. The electroporation therapy apparatus of claim 9, wherein the electroporation generator is configured to calculate the asymmetric balanced waveform to minimize a neurostimulation of the target tissue.

11. The method of claim 1, wherein the electroporation generator is configured to determine whether neurostimulation will occur using the equation $$\forall t \in [0, \tau_{chron}]: \int_0^t E_m \, d\tau = \int_0^t \frac{1}{a_m} \Phi_m \, d\tau < S_{threshold},$$

in which $\tau_{chron}$ is chronaxie time, $E_m$ is an applied electrical field over a membrane of the target tissue, $a_m$ is a thickness of the membrane, $\Phi_m$ is n voltage over the membrane, and $S_{threshold}$ is stimulation threshold.

12. A method of applying irreversible electroporation to a target tissue, comprising:

sending an asymmetric balanced waveform from an electroporation generator to a medical device comprising an electrode assembly having a plurality of electrode elements, wherein the electroporation generator is configured to receive a signal for identifying which pairs of the plurality of electrode elements have electrical characteristics indicative of contact with the target tissue when the target tissue is energized with an excitation signal, and wherein the electroporation generator is configured and to use an electroporation energization strategy to energize at least one of the pairs of the plurality of electrode elements identified as having contact with the target tissue with the asymmetric balanced waveform, wherein the asymmetric balanced waveform comprises a first positive phase and a first negative phase, wherein the first positive phase comprises a first current and a first time and wherein the first negative phase comprises a second current and a second time, wherein the first current is greater than the second current and wherein the second time is greater than the first time, and wherein the asymmetric balanced waveform is configured to enhance electroporation in a non-linear manner while also minimizing neurostimulation of the target tissue, and wherein the asymmetric balanced waveform is further configured to provide a production rate of new pores that is enhanced in a non-linear manner when a time duration of a transmembrane voltage is reduced by a factor 2 and an amplitude of the transmembrane voltage is multiplied by a factor 2.

13. The method of claim 12, wherein the first positive phase and the first negative phase comprises a cycle and wherein the electroporation generator is configured to output a plurality of cycles to the target tissue.

14. The method of claim 13, wherein the electroporation generator is configured to insert a latency period between the first positive phase and the first negative phase and between each of the plurality of cycles.

15. The method of claim 14, wherein the latency period between each of the plurality of cycles is less than 0.5 seconds.

16. The method of claim 13, wherein a combined area of each positive phase and each negative phase in each of the plurality of cycles is near zero.

17. The method of claim 13, wherein the plurality of cycles is configured to apply an applied current function to the target tissue.

18. The method of claim 12, wherein the electroporation generator is configured to calculate the asymmetric balanced waveform to minimize a neurostimulation of the target tissue.

19. The method of claim 12, wherein the electroporation generator is configured to determine whether neurostimulation will occur using the equation $$\forall t \in [0, \tau_{chron}]: \int_0^t E_m \, d\tau = \int_0^t \frac{1}{a_m} \Phi_m \, d\tau < S_{threshold},$$

in which $\tau_{chron}$ is chronaxie time, $E_m$ is an applied electrical field over a membrane of the target tissue, $a_m$ is a thickness of the membrane, $\Phi_m$ is n voltage over the membrane, and $S_{threshold}$ is stimulation threshold.

20. An electroporation therapy system, comprising:

a medical device comprising a plurality of electrode elements; and an electroporation generator, wherein the electroporation generator is configured to output an asymmetric balanced waveform to the plurality of electrode elements, and wherein the electroporation generator is further configured to receive a signal for identifying which pairs of the plurality of electrode elements have electrical characteristics indicative of contact with a target tissue when the target tissue is energized with an excitation signal, and wherein the electroporation generator is configured to use an electroporation energization strategy to energize at least one of the pairs of the plurality of electrode elements identified as having contact with the target tissue with the asymmetric balanced waveform, wherein the asymmetric balanced waveform comprises a first positive phase and a first negative phase, wherein the first positive phase comprises a first current and a first time and wherein the first negative phase comprises a second current and a second time, wherein the first current is greater than the second current and wherein the second time is greater than the first time, and wherein the asymmetric balanced waveform configured to irreversibly electroporate the target tissue, and wherein the electroporation generator is configured to determine whether neurostimulation will occur using the equation $$\forall t \in [0, \tau_{chron}]: \int_0^\tau E_m \, d\tau = \int_0^\tau \frac{1}{a_m} \Phi_m \, d\tau < S_{threshold},$$

in which $\tau_{chron}$ is chronaxie time, $E_m$ is an applied electrical field over a membrane of the target tissue, $a_m$ is a thickness of the membrane, $\Phi_m$ is a voltage over the membrane, and $S_{threshold}$ is stimulation threshold.

* * * * *